United States Patent
Kauppinen et al.

(10) Patent No.: US 6,200,792 B1
(45) Date of Patent: *Mar. 13, 2001

(54) ENZYMES WITH AMINOPEPTIDASE ACTIVITY

(75) Inventors: Markus Sakari Kauppinen; Joan Qi Si; Tina Spendler; Claus Dambmann; Torben Halkier; Peter Rahbek Østergaard; Shamkant Anant Patkar; Kim Hansen, all of Bagsværd (DK)

(73) Assignee: Novo Nordisk-A/S Novo Alle, Bagsuaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/580,064

(22) Filed: May 30, 2000

Related U.S. Application Data

(62) Division of application No. 09/342,394, filed on Jun. 29, 1999, which is a division of application No. 08/929,922, filed as application No. PCT/DK96/00104 on Mar. 15, 1996, now Pat. No. 5,994,113.

(30) Foreign Application Priority Data

Mar. 16, 1995 (DK) .................................................. 0262/95

(51) Int. Cl.⁷ ..................................................... C12N 9/48
(52) U.S. Cl. ........................ 435/212; 536/23.2; 536/23.7
(58) Field of Search .................................... 435/212, 219, 435/223, 224, 225; 536/23.2, 23.7

(56) References Cited

U.S. PATENT DOCUMENTS 5,112,812   5/1992   Samuelsson et al. .................. 514/21

FOREIGN PATENT DOCUMENTS

| 0 065 663 | 12/1982 | (EP) . |
| 0 325 986 | 1/1988 | (EP) . |
| 0 257 821 | 3/1988 | (EP) . |
| WO 94/26882 | 11/1994 | (WO) . |

OTHER PUBLICATIONS

Lehamann et al. "Aminopeptidase aus Aspergilli, I" Hoppe–Seyler's Z. Physiol. Chem. 350 (19), 99–104, Feb. 1969.*
Labbe et al. "Isolement de fractions a activite aminopeptidase . . ." Biochemie 56, 839–844, 1974.*
Matsuoka et al., J. Argric. Food Chem., vol. 39, pp. 1392–1395 (1991).
Nakadai, Arg. Biol. Chem., vol. 37, No. 4, pp. 757–765 (1973),

* cited by examiner

*Primary Examiner*—Nashaat T. Nashed
(74) *Attorney, Agent, or Firm*—Elias J. Lambiris, Esq.

(57) ABSTRACT

The present invention relates to an enzyme exhibiting aminopeptidase activity, a method for producing said enzyme, an enzyme preparation containing said enzyme exhibiting aminopeptidase activity, and use of said enzyme for various industrial purposes.

7 Claims, 1 Drawing Sheet

ENZYMES WITH AMINOPEPTIDASE ACTIVITY

CROSS-REFERENCE TO RELATED APPLICATIONS

This application is a divisional of application Ser. No. 09/342,394 filed on Jun. 29, 1999, which is a divisional of application Ser. No. 08/929,922 filed on Sep. 15, 1997, now issued U.S. Pat. No. 5,994,113, which is a national stage application of PCT/DK96/00104 filed on Mar. 15, 1996, and claims priority under 35 U.S.C. 119 of Danish application no. 0262/95 filed on Mar. 16, 1995, the contents of which are fully incorporated herein by reference.

FIELD OF THE INVENTION

The present invention relates to an enzyme exhibiting aminopeptidase activity, a method for producing said enzyme, an enzyme preparation containing said enzyme exhibiting aminopeptidase activity, and use of said enzyme for various industrial purposes.

BACKGROUND OF THE INVENTION

Protein hydrolysates are being used in numerous food products. Traditionally protein hydrolysates were produced by acid hydrolysis, but today enzymatic hydrolysis is regarded as an attractive alternative.

One of the main problems of protein hydrolysates is that they often taste bitter. When using e.g. soy protein or casein, which are rich in hydrophobic L-amino acids, as the protein source, the protein hydrolysate tends to have bitter taste. In general it is believed that whether the taste of proteins is bitter or not depends on the average hydrophobicity of the L-amino acid residues, such as valine, leucine, isoleucine, phenylalanine, tyrosine and tryptophan.

A vast number of enzymes exhibiting peptidase activity are capable of performing enzymatic hydrolysis on vegetable, yeast and/or animal proteins, resulting in highly nutritious protein hydrolysates useful as food additives in products such as soups, sauces, gravies, paste, tofu, bouillon, seasonings, baby formulas, snacks, ready-to-eat meals etc.

Peptidases

All peptidases or proteases are hydrolases which act on proteins or its partial hydrolysate to decompose the peptide bond.

EP 427,385 (The Japanese R & D Association) discloses a genomic gene encoding an alkaline protease derived from yellow molds such as *Aspergillus oryzae*.

JP-0-2002374 and JP-0-2002375 (Shokuhin), describes an alkaline protease derived from *Aspergillus oryzae* for use in medicine, food, and detergents.

SU-891777 (Khark) concerns a microbial protease from *Aspergillus oryzae*, which can be used in food, medicine etc.

JP-5-4035283 (Ajinomoto KK) discloses preparation of enzymes from e.g. *Aspergillus oryzae* exhibiting endopeptidase activity, which can hydrolyse proteins almost completely.

WO 94/25580 (Novo Nordisk A/S) describes a method for hydrolysing vegetable or animal protein by incubating with a proteolytic enzyme preparation derived from a strain of *Aspergillus oryzae*.

Aminopeptidases

A subgroup of peptidases (proteases) are called aminopeptidases and are classified under the Enzyme Classification number E.C. 3.4.11 (aminopeptidases) in accordance with the Recommendations (1992) of the International Union of Biochemistry and Molecular Biology (IUBMB)).

Aminopeptidases are capable of removing one or more amino terminal residues from polypeptides.

JP-7-5034631 (Noda) discloses a leucine aminopeptidase derived from yellow koji mold, which includes *Aspergillus oryzae*.

JP-7-4021798 (Zaidan Hojin Noda Sangyo) describes the production of miso by adding of a leucine aminopeptidase II prepared by cultivating a number of molds, including *Aspergillus oryzae* strain 460 and strain IAM 2616.

Van Heeke et al., Bioch. Biophys. Acta, (1992), 1131, 337–340, have disclosed the cloning of a 30 kDa aminopeptidase from the bacteria *Vibrio proteolyticus* deposited at the American Type Culture Collection under the ATCC No. 15338.

*Aspergillus oryzae* 460 is known to produce a number of leucine aminopeptidases. The molecular weight of three of these was calculated to 26,500, 56,000 and 61,000, respectively determined by gel filtration (Nakada et al., Agr. Biol. Chem, (1972), 37(4), 757–765; Nakada et al., Agr. Biol. Chem, (1972), 37(4), 767–774; Nakada et al., Agr. Biol. Chem, (1972), 37(4), 775–782). The *Aspergillus oryzae* 460 strain is deposited at the American Type Culture Collection as *A. oryzae* (AT7C no. 20386).

Reduction of bitter taste of protein hydrolysates

EP 65,663 and EP 325,986 (Miles Inc.) concerns enzymatic hydrolysis of proteins using a mixture of enzymes containing *Aspergillus oryzae* derived proteases. The obtained protein hydrolysate has a bland, non-bitter taste.

JP47029577 (Asahi Electro-chemical Co.) concerns a protease, derived from *Aspergillus oryzae*, which does not produce any bitter component when decomposing protein.

Prior art discloses a plethora of enzymes exhibiting peptidase, aminopeptidase and other enzyme activities. Said enzymes may be derived from a number of microorganisms, including the fungus species *Aspergillus oryzae*.

In general products, useful for producing protein hydrolysates without a bitter taste, comprise a mixture of peptidase and aminopeptidase activities.

It would therefore be desirable to be able to provide a single-component enzyme (i.e. substantially without any side activity) exhibiting only an activity useful for reducing the bitterness of protein hydrolysates used in food products.

SUMMARY OF THE INVENTION

Figure 1:
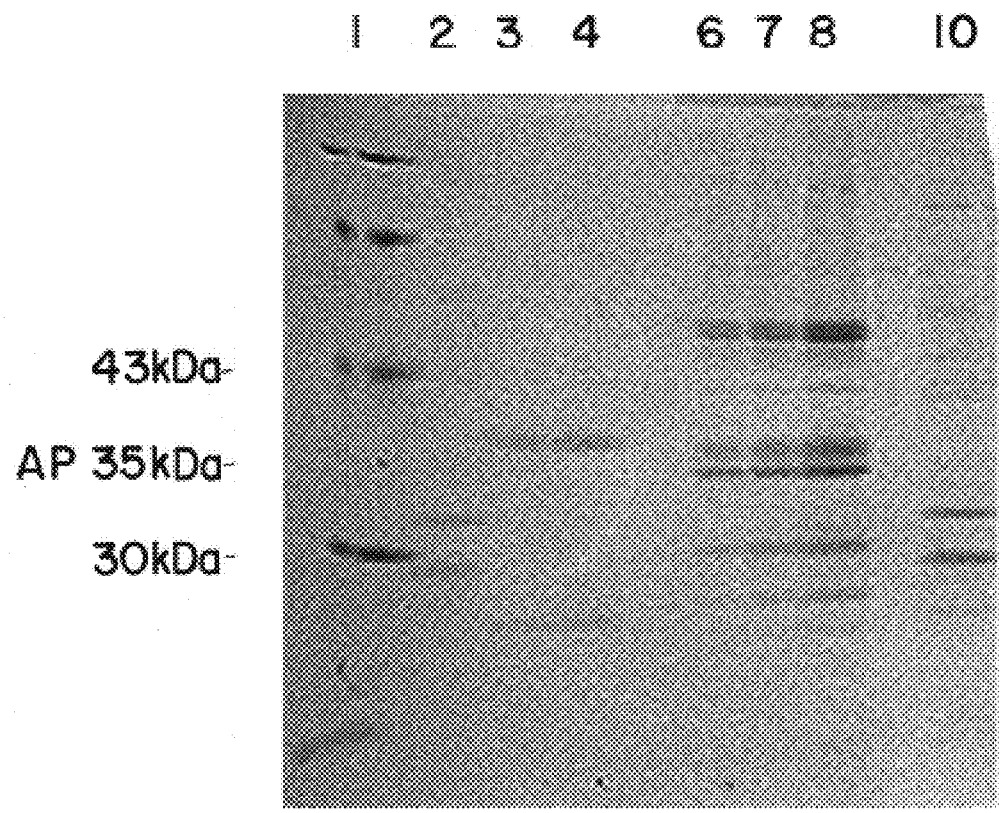
FIG. 1 shows the result of SDS-PAGE analysis of supernatant from the *Aspergillus oryzae* A01568 35 kDa aminopeptidase producing transformant.

The object of the present invention is to provide a single-component enzyme exhibiting an activity, which is particularly useful for preparing improving bread products and for producing proteins and/or protein hydrolysates without bitter taste for foodstuff.

The present inventors have surprisingly succeeded in isolating a DNA sequence encoding an enzyme exhibiting aminopeptidase activity, which advantageously may be used for improving the flavour, crust colour, crumb structure and dough stickiness of baked products. Further, said novel enzyme is useful for producing protein or protein hydrolysates without bitter taste.

The complete DNA sequence encoding said aminopeptidase makes it possible to prepare single-component aminopeptidases.

The complete DNA sequence, shown in SEQ ID no. 1, encoding the aminopeptidase of the invention has, comprised in a plasmid, been transformed into the bacteria strain *Escherichia coli* DSM no. 9965. This will be described further below.

By a database alignment search it was found that the DNA sequence shown in SEQ ID No. 1 is novel. The highest degree of similarity and identity was found to be 53% and 32%, respectively, to the above mentioned 30 kDa aminopeptidase froim the bacteria *Vibrio proteolyticus* (ATCC No. 15338).

The inventors have characterized the precursor-form of the aminopeptidase consisting of a secretion signal and the 35 kDa aminopeptidase. The molecular weight ($M_w$) of the precursor-form was calculated to 41 kDa, and the isoelectric point (p1) was estimated to be approximately 4.9. Further, the amino acid composition of the aminopeptidase was estimated as shown in Table 1.

TABLE 1

| | No. | Percent |
|---|---|---|
| Non-polar: | | |
| Ala | 37 | 9.79 |
| Val | 23 | 6.08 |
| Leu | 29 | 7.67 |
| Ile | 20 | 5.29 |
| Pro | 14 | 3.70 |
| Met | 3 | 0.79 |
| Phe | 19 | 5.03 |
| Trp | 2 | 0.53 |
| Polar: | | |
| Gly | 28 | 7.41 |
| Ser | 32 | 8.47 |
| Thr | 25 | 6.61 |
| Cys | 4 | 1.06 |
| Tyr | 13 | 3.44 |
| Asn | 11 | 2.91 |
| Gln | 16 | 4.23 |
| Acidic: | | |
| Asp | 29 | 7.67 |
| Glu | 25 | 6.61 |
| Basic: | | |
| Lys | 28 | 7.41 |
| Arg | 9 | 2.38 |
| His | 10 | 2.65 |

The deduced complete precursor-form of the amino acid sequence of the 35 kDa enzyme is shown in SEQ ID No. 2.

Accordingly, the first aspect of the invention relates to an enzyme exhibiting aminopeptidase activity having an apparent molecular weight ($M_w$) of about 35 kDa determined by SDS-PAGE.

Mass spectrometry showed that the average mass of the recombinant aminopeptidase is in the range from 33 kDa to 35 kDa.

The isoelectric point (pI) of the enzyme was determined to be about 4.9.

The isoelectric point, pI, is defined as the pH value where the enzyme molecule complex (with optionally attached metal or other ions) is neutral, i.e. the sum of electrostatic charges (net electrostatic charge, NEC) on the complex is equal to zero. In this sum of course consideration of the positive or negative nature of the electrostatic charge must be taken into account.

In the following the terms "35 kDa aminopeptidase" and "the enzyme exhibiting aminopeptidase activity" are used interchangeably for the single-component enzyme of the present invention.

The enzyme exhibiting aminopeptidase activity of the invention may be derived from a number of microorganisms. The present inventors have isolated the aminopeptidase of the invention from the filamentous fungus *Aspergillus oryzae* A01568, which is a strain deposited at the American Type Culture Collection as *Aspergillus oryzae* 460 (FERM-P no. 1149, ATCC no. 20386, and further described in U.S. Pat. No. 3,914,436.

The enzyme exhibiting aminopeptidase activity of the invention comprises at least one of the partial amino acid sequences shown in SEQ ID Nos. 6, 7, 8, 9, and 10, respectively. SEQ ID No 11 is a peptide (5) which overlaps and extends the N-terminal sequence.

In the second aspect, the invention-relates to a DNA construct comprising a DNA sequence encoding said aminopeptidase, which DNA sequence comprises a) the aminopeptidase encoding part of the DNA sequence shown in SEQ ID No. 1, and/or the DNA sequence obtainable from *E. coli* DSM 9965, or b) an analogue of the DNA sequence shown defined in a), which i) is homologous with the DNA sequence shown in SEQ ID No. 1 and/or the DNA sequence obtainable from *E. coli* DSM 9965, or ii) hybridizes with the same oligonucleotide probe as the DNA sequence shown in SEQ ID No. 1 and/or the DNA sequence obtainable from *E. coli* DSM 9965, or iii) encodes a polypeptide which is homologous with the polypeptide encoded by a DNA sequence comprising the DNA sequence shown in SEQ ID No. 1 and/or the DNA sequence obtainable from *E. coli* DSM 9965, or iv) encodes a polypeptide which is immunologically reactive with an antibody raised against the purified aminopeptidase encoded by the DNA sequence shown in SEQ ID No 1 derived from *Aspergillus oryzae* A01568 or obtainable from *E. coli*, DSM 9965.

In the present context, the "analogue" of the DNA sequence shown in SEQ ID No. 1 and/or the DNA sequence obtainable from *E. coli* DSM 9965, is intended to indicate any DNA sequence encoding an enzyme exhibiting aminopeptidase activity, which has at least one of the properties i)–iv).

The analogous DNA sequence may be isolated from another or related (e.g. the same) organism producing the enzyme exhibiting aminopeptidase activity on the basis of any of the DNA sequences shown in SEQ ID Nos. 3–5, e.g. using the procedures described herein, and thus, e.g. be an allelic or species variant of the DNA sequence comprising the DNA sequences shown herein, may be constructed on the basis of any of the DNA-sequences shown in SEQ ID Nos. 3–5, e.g. by introduction of nucleotide substitutions which do not give rise to another amino acid sequence of the aminopeptidase encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, that is conservative amino acid substitutions that do not significantly affect the folding or activity of the polypeptide, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., (1991), Protein Expression and Purification 2, 95–107. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active enzyme. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, (1989), Science 244, 1081–1085). In the latter technique mutations are introduced at every residue in the molecule, and the resulting mutant molecules are tested for biological (i.e. aminopeptidolytic) activity to identify amino acid residues that are critical to the activity of the molecule. Sites of substrate-enzyme interaction can also be determined by analysis of crystal structure as determined by such techniques as nuclear magnetic resonance, crystallography or photoaffinity labelling. See, for example, de Vos et al. (1992), Science 255, 306–312; Smith et al., (1992), J. Mol. Biol., 224, 899–904; Wlodaver et al., (1992), FEBS Lett., 309, 59–64.

It will be understood that the DNA sequences shown in SEQ ID Nos. 3–5 are sequences which may be used for isolating the entire DNA sequence encoding the aminopeptidase, e.g. the DNA sequence shown in SEQ ID No. 1 and/or the DNA sequence transformed into the deposited strain *E. coli* DSM 9965. The term "analogue" is intended to include said entire DNA sequence, which comprises one or more of the partial sequences shown in SEQ ID Nos. 3–5 or parts thereof. The amino acid sequence (as deduced from the DNA sequence shown in SEQ ID No. 1) is shown in SEQ ID No. 2.

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology, 48, p. 443453). Using GAP with the following settings for DNA sequence comparison: GAP creation penalty of 5.0 and GAP extension penalty of 0.3, the coding region of the DNA sequence exhibits a degree of identity preferably of at least at least 70%, preferably at least 80%, especially at least 90%, with the coding region of the DNA sequence shown in SEQ ID No. 1 or the DNA sequence obtainable from the plasmid in *E. coli* DSM 9965.

The hybridization referred to in ii) above is intended to indicate that the analogous DNA sequence hybridizes to the same probe as the DNA sequence encoding the aminopeptidase under certain specified conditions which are described in detail in the Materials and Methods section hereinafter.

Normally, the analogous DNA sequence is highly homologous to the DNA sequence such as at least 60% homologous to the DNA sequence shown in SEQ ID No. 1 or the DNA sequence obtainable from the plasmid in *E. coli* DSM 9965 encoding an aminopeptidase of the invention, such as at least 65%, at least 70%, at least 75%, at least 80%, at least 85%, at least 90% or even at least 95% homologous to said DNA sequence.

The homology referred to in iii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology, 48, p. 443–453). Using GAP with the following settings for DNA sequence comparison: GAP creation penalty of 5.0 and GAP extension penalty of 0.3, the coding region of the DNA sequence exhibits a degree of identity preferably of at least at least 70%, preferably at least 80%, especially at least 90%, with the coding region of the DNA sequence shown in SEQ ID No. 1 or the DNA sequence obtainable from the plasmid in *E. coli* DSM 9965.

The term "derived from" in connection with property iv) above is intended not only to indicate an aminopeptidase produced by strain A01568, but also an aminopeptidase encoded by a DNA sequence isolated from strain A01568 and produced in a host organism transformed with said DNA sequence. The immunological reactivity may be determined by the method described in the "Materials and Methods" section below.

In farther aspects the invention relates to an expression vector harbouring a DNA construct of the invention, a cell comprising the DNA construct or expression vector and a method of producing an enzyme exhibiting aminopeptidase activity which method comprises culturing said cell under conditions permitting the production of the enzyme, and recovering the enzyme from the culture.

It is also an object of the invention to provide an enzyme preparation enriched with the 35 kDa aminopeptidase of the invention.

Further, the invention provides a bread-improving or a dough-improving composition comprising an enzyme exhibiting aminopeptidase activity of the invention. Said composition may be combined with other enzymes, such as amylolytic enzymes, and conventional bread improving agents.

In a still further aspect the invention relates to a method for preparing a baked product and frozen dough comprising the 35 kDa aminopeptidase of the invention.

Finally the invention relates to the use of the 35 kDa aminopeptidase of the invention. The enzyme of the invention or a composition of the invention comprising such an enzyme may be used for improving the flavour, crust colour and crumb structure of baked products and to improve the stickiness of frozen dough. The aminopeptidase of the invention may furthermore be used advantageously in connection with producing proteins and protein hydrolysates without bitter taste and may be used for a number of purposes including, degradation or modification of protein containing substances; cleaning of contact lenses, preparation of food and animal feed etc.

DETAILED DESCRIPTION OF THE INVENTION

The DNA sequence of the invention encoding an enzyme exhibiting aminopeptidase activity may be isolated by a general method involving cloning, in suitable vectors, a DNA library from *Aspergillus oryzae*, transforming suitable yeast host cells with said vectors, culturing the host cells under suitable conditions to express any enzyme of interest encoded by a clone in the DNA library, screening for positive clones by determining any aminopeptidase activity of the enzyme produced by such clones, and isolating the DNA coding an enzyme from such clones.

The general method is further disclosed in WO 93/11249 the contents of which are hereby incorporated by reference. A more detailed description of the screening method is given in Example 3 below.

Microbial Sources

The DNA sequence coding for the aminopeptidase of the invention may for instance be isolated by screening a cDNA library of the donor organism, and selecting for clones expressing the appropriate enzyme activity (i.e. aminopeptidase activity as defined by the ability of the enzyme to hydrolyse Leucine-7 amido-4-methylcoumarin). The appropriate DNA sequence may then be isolated from the clone by standard procedures, e.g. as described in Example 1.

The donor organism may be a fungus of the Aspergillus oryzae (ATCC no. 20386) described in U.S. Pat. No. 3,914,436

The complete full length DNA sequence encoding the aminopeptidase of the invention has been transformed into a strain of the bacteria *E. coli,* comprised in the expression plasmid pYES 2.0 (Invitrogen). Said bacteria has been deposited by the inventors according to the Budapest Treaty on the International Recognition of the Deposit of Microorganisms for the Purposes of Patent Procedure at the Deutshe Sammlung von Mikroorganismen und Zellkulturen GmbH., Mascheroder Weg 1b, D-38124 Braunschweig Federal Republic of Germany, (DSM).

Deposit date: 11.05.95

Depositor's ref.: NN49001

DSM designation: *E. coli* DSM No. 9965

Being an International Depository Authority under the Budapest Treaty, Deutshe Sammlung von Mikroorganismen und Zellkulturen GmbH., affords permanence of the deposit in accordance with the rules and regulations of said treaty, vide in particular Rule 9. Access to the two deposits will be available during the pendency of this patent application to one determined by the Commisioner of the United States Patent and Trademark Office to be entitled thereto under 37 C.F.R. Par. 1.14 and 35 U.S.C. Par. 122. Also, the above mentioned deposits fulfil the requirements of European patent applications relating to microorganisms according to Rule 28 EPC.

The above mentioned deposit represents a substantially pure culture of the isolated bacteria. The deposit is available as required by foreign patent laws in countries wherein counterparts of the subject application, or its progeny are filed. However, it should be understood that the availability of the deposited strain does not constitute a license to practice the subject invention in derogation of patent rights granted by governmental action.

The DNA sequence encoding the enzyme exhibiting aminopeptidase activity can for instance be isolated from the above mentioned deposited strain by standard methods.

It is expected that a DNA sequence coding for a homologous enzyme, i.e. an analogous DNA sequence, is obtainable from other microorganisms. For instance, the DNA sequence may be derived by similarly screening a cDNA library of another microorganism, in particular a fungus, such as a strain of an Aspergillus sp., in particular a strain of *A. aculeatus* or *A. niger,* a strain of another Trichoderma sp., in particular a strain of *T. reesei, T. viride, T. longibrachiatum* or *T. koningii* or a strain of a Fusarium sp., in particular a strain of *F. oxysporum,* or a strain of a Humicola sp.

Alternatively, the DNA sequence coding for an enzyme exhibiting aminopeptidase activity of the invention may, in accordance with well-known procedures, conveniently be isolated from DNA from a suitable source, such as any of the above mentioned organisms, by use of synthetic oligonucleotide probes prepared on the basis of a DNA sequence disclosed herein. For instance, a suitable oligonucleotide probe may be prepared on the basis of any of the nucleotide sequences shown in SEQ ID Nos. 3–5 or the amino acid sequence shown in SEQ ID No. 2 or any suitable subsequence thereof.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the aminopeptidase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the aminopeptidase, the promoter and the terminator, respectively, and to insert them into suitable vectors are well known to persons skilled in the art (cf., for instance, Sambrook et al., (1989), Molecular Cloning. A Laboratory Manual, Cold Spring Harbor, N.Y.).

The host cell which is transformed with the DNA sequence encoding the enzyme of the invention is preferably an eukaryotic cell, in particular a fungal cell such as a yeast or filamentous fungal cell. In particular, the cell may belong to a species of Aspergillus, most preferably *Aspergillus oryzae* or *Aspergillus niger.* Fungal cells may be transformed by a process involving protoplast formation and transformation of the protoplasts followed by regeneration of the cell wall in a manner known per se. The use of Aspergillus as a host microorganism is described in EP 238 023 (Novo Nordisk A/S), the contents of which are hereby incorporated by reference. The host cell may also be a yeast cell, e.g. a strain of Saccharomyces, in particular *Saccharomyces cerevisiae, Saccharomyces kluyveri* or *Saccharomyces uvanim,* a strain of Schizosaccharonzyces sp., such as *Schizosaccharonryces pombe,* a strain of Hansenula sp. Pichia sp., Yarrowia sp. such as *Yarrowia lipolytica,* or Kluyveroniyces sp. such as *Kluyveronyces lactis.*

A method of producing an enzyme of the invention

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed aminopeptidase may conveniently be secreted into the culture medium and may be recovered there from by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme preparation

In a still further aspect, the present invention relates to an enzyme preparation useful for reducing the bitterness of proteins and/or protein hydrolysates for foodstuff.

The enzyme preparation, having been enriched with an enzyme of the invention, may e.g. be an enzyme preparation comprising multiple enzymatic activities, such as an enzyme preparation comprising multiple enzymes for producing protein hydrolysates. The preparation to be enriched can be Flavourzyme® (available from Novo Nordisk A/S). Flavourzyme® is a protease/peptidase complex derived from Aspergillus oryzae developed for hydrolysis of proteins.

Dependent on the use for which the enzyme preparation is to be used the aminopeptidase of the invention may be combined with other enzyme as mentioned below.

In the present context, the term "enriched" is intended to indicate that the aminopeptidase activity of the enzyme preparation has been increased, e.g. with an enrichment factor of at least 1.1, preferable between 1.1 and 10, more preferred between 2 and 8, especially between 4 and 6, conveniently due to addition of an enzyme of the invention prepared by the method described above.

Alternatively, the enzyme preparation enriched with an enzyme exhibiting aminopeptidase activity may be one which comprises an enzyme of the invention as the major enzymatic component, e.g. a single-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

In another aspect the invention relates to a bread-improving or a dough-improving composition comprising an aminopeptidase of the invention. Said composition may further comprise enzymes selected from the group including amylolytic enzyme, such as α-amylase, β-amylase, maltogenic α-amylase, amyloglucosidase, acid stable amylase, and 1,6-pullulanase.

Such enzymes are available from Novo Nordisk A/S as AMG™ (amyloglucosidase) obtained from a strain of *Aspergillus niger*, Fungamyl™ (fungal amylase) obtained from a strain of *Aspergillus oryzae*, Novamyl™ (maltogenic amylase) obtained from a strain of *Bacillus stearothermophilus*.

The composition of the invention may also comprise one or more additional enzymes. Examples of such enzymes include a cellulase, a hemicellulase, a pentosanase (useful for the partial hydrolysis of pentosans which increases the extensibility of the dough), a lipase (useful for modification of lipids present in the dough or dough constituents so as to soften the dough), a peroxidase (useful for improving the dough consistency), an oxidase, e.g. a glucose oxidase, a laccase, a xylanase, a protease (useful for gluten weakening, in particular when using hard wheat flour).

The other enzyme components are preferably of microbial origin and may be obtained by conventional techniques used in the art as mentioned above.

The enzyme(s) to be used in the present invention may be in any form suited for the use in question, e.g. in the form of a dry powder or granulate, in particular a non-dusting granulate, a liquid, in particular a stabilized liquid, or a protected enzyme. Granulates may be produced, e.g. as disclosed in U.S. Pat. No. 4,106,991 and U.S. Pat. No. 4,661,452 (both to Novo Industri A/S), and may optionally be coated by methods known in the art. Liquid enzyme preparations may, for instance, be stabilized by adding nutritionally acceptable stabilizers such as a sugar, a sugar alcohol or another polyol, lactic acid or another organic acid according to established methods. Protected enzymes may be prepared according to the method disclosed in EP 238, 216.

Normally, for inclusion in pre-mixes or flour it is advantageous that the enzyme(s) is/are in the form of a dry product, e.g. a non-dusting granulate, whereas for inclusion together with a liquid it is advantageously in a liquid form.

In addition or in an alternative to other enzyme components, the dough-improving and/or bread-improving composition may comprise a conventionally used baking agent, e.g. one or more of the following constituents:

A milk powder (providing crust colour), gluten (to improve the gas retention power of weak flours), an emulsifier (to improve dough extensibility and to some extent the consistency of the resulting bread), granulated fat (for dough softening and consistency of bread), an oxidant (added to strengthen the gluten structure; e.g. ascorbic acid, potassium bromate, potassium iodate or ammonium persulfate), an amino acid (e.g. cysteine), a sugar, and salt (e.g. sodium chloride, calcium acetate, sodium sulfate or calcium sulphate serving to make the dough firmer), flour or starch. Such components may also be added directly to the dough in accordance with a method of the invention.

Examples of suitable emulsifiers are mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, phospholipids and lecithin.

The bread-improving and/or dough improving composition of the invention is typically included in the dough in an amount corresponding to 0.01–5%, in particular 0.1–3%.

In accordance with the method of the invention, in which an enzyme with aminopeptidase activity of the invention, optionally in combination with other enzymes as described above, is used for the preparation of dough and/or baked products, the enzyme(s) may be added as such to the mixture from which the dough is made or to any ingredient, e.g. flour, from which the dough is to be made. Alternatively, the enzyme(s) may be added as a constituent of a dough-improving and/or a bread-improving composition as described above, either to flour or other dough ingredients or directly to the mixture from which the dough is to be made.

The dosage of the enzyme(s) to be used in the method of the present invention should be adapted to the nature and composition of the dough in question as well as to the nature of the enzyme(s) to be used. Normally, the enzyme preparation is added in an amount corresponding to 0.01–1000 mg enzyme protein per kg of flour, preferably 0.1–100 mg enzyme protein per kg of flour, more preferably 0.1–10 mg enzyme protein per kg of flour.

In terms of enzyme activity, the appropriate dosage of a given single component enzyme with aminopeptidase activity, optionally in combination with other enzyme(s), for exerting a desirable improvement of flour or crust colour of a baked product will depend on the enzyme(s) and the enzyme substrate(s) in question. The optimal dosage may vary dependent on the flour or yeast types and baking process. The skilled person may determine a suitable enzyme unity dosage on the basis of methods known in the art.

However, according to the present invention the enzyme exhibiting aminopeptidase activity of the invention is added in an amount corresponding 30 to 1000 LAPU, preferably 50 to 500 LAPU, especially 80 to 300 LAPU, such as about 100 LAPU per kg of flour. LAPU is defined below.

Amylolytic enzymes are normally added in from 1 to 50 FAU per kg flour. One FAU (Fungal α-Amylase Unit) is the amount of enzyme which breaks down 5.26 g starch (Merck, Amylum solubile Erg. B.6, BAch 9947275) per hour using Novo Nordisk's standard method for determination of αamylase activity. A detailed description of Novo Nordisk's method (AF 216) of analysis is available on request.

Maltogenic amylase are normally added in from 1 to 1000 MANU per kg flour (Maltogenic Amylase Novo Units). One MANU is defined as the amount of enzyme which, under standard conditions, hydrolyzes i micromole of maltotriose per minute. The analytic method (AF 203) is available on request.

When one or more additional enzyme activities are to be added in accordance with the method of the invention, these activities may be added separately or together with the singes component enzyme with exopeptidase activity, optionally as constituent(s) of the bread-improving and/or dough-improving composition of the invention. The other enzyme activities may be any of the above described enzymes and may be dosed in accordance with established baking practice.

As mentioned above the enzyme exhibiting aminopeptidase activity, optionally in combination with other enzyme (s) as described above, is added to any mixture of dough ingredients, to the dough, or to any of the ingredients to be included in the dough, in other words the enzyme(s) may be added in any step of the dough preparation and may be added in one, two or more steps, where appropriate.

The handling of the dough and/or baking is performed in any suitable manner for the dough and/or baked product in question, typically including the steps of kneading the dough, subjecting the dough to one or more proofing treatments, and baking the product under suitable conditions, i.e. at a suitable temperature and for a sufficient period of time. For instance, the dough may be prepared by using a normal straight dough process, a sour dough process, an overnight dough method, a low-temperature and long-time fermentation method, a frozen dough method, the Chorleywood Bread process, or the Sponge and Dough process.

The dough and/or baked product prepared by the method of the invention are normally based on wheat meal or flour, optionally in combination with other types of meal or flour such as corn flour, rye meal, rye flour, oat flour or meal, soy flour, sorghum meal or flour, or potato meal or flour.

In the present context the term "baked product" is intended to include any product prepared from dough, either of a soft or a crisp character. Examples of baked products, whether of a white, light or dark type, which may advantageously be produced by the present invention are bread (in particular white, whole-meal or rye bread), typically in the form of loaves or rolls, French baguette-type bread, pita bread, tacos, cakes, pan-cakes, biscuits, crisp bread and the like.

The dough of the invention may be of any of the types discussed above, and may be fresh or frozen.

The preparation of frozen dough is described by K. Kulp and K. Lorenz in "Frozen and Refrigerated Doughs and Batters". When using the aminopeptidase of the invention for frozen bread the flavour, the crust colour and the crispiness are improved.

From the above disclosure it will be apparent that the dough of the invention is normally a leavened dough or a dough to be subjected to leavening. The dough may be leavened in various ways such as by adding sodium bicarbonate or the like or by adding a leaven (fermenting dough), but it is preferred to leaven the dough by adding a suitable yeast culture such as a culture of *Saccharomyces cerevisiae* (baker's yeast). Any of the commercially available *S. cerevisiae* strains may be employed.

As mentioned above, the present invention further relates to a pre-mix, e.g., in the form of a flour composition, for dough and or baked products made from dough, which pre-mix comprises an enzyme exhibiting aminopeptidase activity of the invention and optionally other enzymes as specified above. The pre-mix may be prepared by mixing the relevant enzyme(s) or a bread-improving and/or dough-improving composition of the invention comprising the enzyme(s) with a suitable carrier such as flour, starch, a sugar or a salt. The pre-mix may contain other dough-improving and/or bread-improving additives, e.g., any of the additives; including enzymes, mentioned above.

Use of the 35 kDa Aminopeptidase of the invention
Use of the Enzyme of the invention for preparing Baked Products The enzyme or an enzyme preparation of the invention may be used in baking, e.g. in order to weaken the gluten components of flour so as to obtain a softening of so-called hard flour.

However, it has surprisingly been found that the aminopeptidase of the invention does not degrade the network of the gluten which is normally observed when proteases are used for preparing baked products. Consequently, the dough characteristics and crumb structure are not affected.

Further, when adding the 35 kDa aminopeptidase of the invention to the dough or dough ingredients, when preparing baked products, the flavour crust colour and/or the crumb structure and/or the crust colour of a baked product will be substantially improved, as shown in Example 13.

Further, the enzyme of the invention improves the dough stickiness.

The addition of the enzyme of the invention results in baked products having a flavour of yeasty type, providing a "freshly baked" bread smell. This make the invention of particular interest for the sponge-dough-system, in which an addition of the enzyme can reduce the sponge fermentation time without a concomitant loss of yeasty flavour, and in the no-time-dough process (most European processes), in which the enzyme can provide a yeasty flavour which is otherwise normally lacking products prepared from such processes.

Without being limited to any theory it is presently believed that further improved flavour and/or crust colour of a baked product may be obtained when a single component enzyme with exopeptidase activity is used in combination with an amylolytic enzyme, in particular an amylolytic enzyme which is capable of liberating reducing sugar molecules from flour or other constituents of the dough. The increased amount of reducing sugars in the dough provides an increase in Maillard reactions taking place during baking thereby further improving the flavour and crust colour of the baked product.

Use of the Enzyme of the invention for Reducing Bitter Taste

The enzyme or enzyme preparation of the invention may be used for reducing the bitterness of proteins and/or protein hydrolysate for foodstuff.

Also contemplated according to the invention is the production of free amino acids from proteins and/or protein hydrolysates. In the case of the free amino acid are glutamine acid it enhances the flavour of food products.

Said protein or protein hydrolysate may be of animal or vegetable origin.

In an embodiment of the invention the protein to be hydrolysed is casein or soy protein.

The protein may be use for producing foodstuff such as cheese and foodstuff containing cocoa.

Even though the aminopeptidase and enzyme preparations enriched with an enzyme of the invention may be used especially advantageously in connection with producing proteins or protein hydrolysates without bitter taste, the aminopeptidase of the invention can be used for a number of industrial applications, including degradation or modification of protein containing substances, such cell walls. Some proteins, like extensins, are components of plant cell walls. Aminopeptidases will therefore facilitate the degradation or modification of plant cell walls.

The dosage of the enzyme preparation of the invention and other conditions under which the preparation is used may be determined on the basis of methods known in the art.

Extraction of Oil from Plants

The enzyme preparation according to the invention may be useful for extraction of oil from plant sources like olives and rape or for production of juice from different fruits like apples, pears and citrus. It may also be useful in the wine industry, especially in the white wine industry, to prevent haze formation. Furthermore, it may be used to modify and degrade proteins, e.g. in order to reduce the viscosity caused or partially caused by proteins, or to facilitate fermentative processes where proteins are involved, or it may be used to improve the digestibility of proteins and other nutrients.

The Use for preparing Food and Feed

The aminopeptidase preparation may also be used in the food and feed industry to improve the digestibility of proteins. For instance, the enzyme or enzyme preparation may be added to animal feed or may be used to process animal feed, in particular feed for piglets or poultry.

Further the enzyme or enzyme preparation of the invention may be useful to make protein hydrolysates from, e.g., vegetable proteins like soy, pea, lupin or rape seed protein, milk like casein, meat proteins, or fish proteins. The aminopeptidase may be used for protein hydrolysates to improve the solubility, consistency or fermentability, to reduce antigenicity or for other purposes to make food, feed or medical products. The aminopeptidase may be used alone or together with other aminopeptidases or together with other enzymes like exopeptidases. The use of the aminopeptidase of the invention together with exopeptidase rich enzyme preparations will improve the taste of the protein hydrolysates.

Furthermore, the enzyme or enzyme preparation may be used in the processing of fish or meat, e.g. to change texture and/or viscosity.

Use in Brewing processes

The enzyme preparation may also be used to facilitate fermentative processes, like yeast fermentation of barley, malt and other raw materials for the production of e.g. beer.

Use for making Protoplast

The enzyme preparation may be useful for making protoplasts from fungi.

Use for the production of Peptides

The enzyme preparation may be useful for production of peptides from proteins, where it is advantageous to use a cloned enzyme essentially free from other proteolytic activities.

Use for degradation of Proteins

Further, the aminopeptidase preparation can be used to degrade protein in order to facilitate purification of or to upgrade different products, like in purification or upgrading of gums, like guar gum, xanthan gum, degumming of silk, or improvement of the quality of wool.

Use for cleaning Contact Lenses

Further the enzyme or enzyme preparation may be used for cleaning of contact lenses.

The invention is described in further detail in the following examples which are not in any way intended to limit the scope of the invention as claimed.

METHODS AND MATERIALS

Materials

Donor organism: *Aspergillus oryzae* A01568 (described in U.S. Pat. No. 3,914,436)

Host organism:

*Escherichia coli* MC1061 (Meissner et al., (1987), Proc. Natl. Acad. Sci. U.S.A., 84, 4171–4176: cDNA library strain

*Saccharomyces cerevisiae* W3124 (van den Hazel et al., (1992), Eur. J. Biochem., 207, 277–283): Activity screening strain.

*Schizosaccharomyces pombe*: Bröker et al., (1989), FEBS Letters, 248, 105–110.

Other organisms:

*Aspergillus oryzae* A1560 (Christensen et al. (1988), Bio/technology 6, 1419–1422).

Plasmids:

pYES 2.0: Transformation vector (Invitrogen).

pHD414: Aspergillus expression vector is a derivative of the plasmid p775 (described in EP 238.023). The construction of the pHD414 is further described in WO 93/11249. pHD414 contains the *A. niger* glucoamylase terminator and the *A. oryzae* TAKA amylase promoter.

pHD423 is a derivative of pHD414 (described in WO 94/20611) with a new polylinker.

pUC18: Expression vector (Sambrook et al., (1989), Molecular Cloning: A Laboratory Manual, 2. ed.; Cold Spring Harbor Laboratory, Cold Spring Harbor, N.Y.)

pC1EXP3: plasmid comprising the 1.4 kb cDNA insert encoding the 35 kDa aminopeptidase of the invention. (See Example 3 and SEQ ID NO 1)

pC1EXP4: plasmid comprising a cDNA sequence, which is 120 bp shorter that the pC1EXP3 1.4 kb cDNA insert. (see Example 10 and SEQ ID NO 12)

p3SR2: *A. nidulans* amdS+ gene carrying plasmid (Christensen et al., (1988), Bio/Technology 6, 1419–1422)

pP1: yeast expression vector, which is an *E. coli/S. pombe*. shuttle vector containing the ADH promoter and URA 3 as selective marker (Broker et al., (1989), FEBS Letters, 248, 105–110).

Primers:

Universal pUC primers (Sambrook et al., (1989), supra)

Deduced primer sequences used in PCR reactions s2:

5'-GAR ACI GTI CAR AAY CTI AT-3' (SEQ ID NO:13)

s3:

5'-GAY AAR AAR AAY TIY GAW ACI GT-3' (SEQ ID NO:14)

as1:

5'-TCI ACR TTR TCI GTI ATI ATY TCI AT-3' (SEQ ID NO:15)

(s=sense, as=anti-sense)

A=Adenine

G=Guanine

C=Cytosine

T=Thymine

I=Deoxyinosine
Y=C or T
R=A or G
W=A or T
Forward and Reverse pYES primers (Invitrogen)
Enzymes:
Lysine-specific protease
Novozym® 234 (Novo Nordisk A/S)
Alcalase® (Novo Nordisk A/S)
Neutrase® (Novo Nordisk A/S)
Peptides of the 35 kDa amrinopeptidase:
(see SEQ ID No. 6–11)
N-terminal:

Direct N-terminal sequencing of authentic and recombinant aminopeptidase revealed the same N-terminal amino acid sequence for the two enzymesvshowing that the recombinant enzyme is proteolytically processed identical to the authentic enzyme. The N-terminal sequence found was

```
Tyr-Pro-Asp-Ser-Val-Gln-His-Xaa-Glu-Thr-Val-Gln-Asn-Leu-Ile-     (SEQ ID NO:10)
                                s2 ----->

Lys-Ser-Leu-Asp-Lys-Lys-Asn-Phe-Glu-Thr-Val-Leu-Gln-Pro-
             s3----->
(Xaa is a glycosylated Asn-residue)
```

The following peptide sequence was obtained from peptides derived from a S-carboxymethylated sample of the aminopeptidase by cleavage with a lysyl-specific protease.

```
Peptide 1:
Tyr-Pro-Asp-Ser-Val-Gln-His-Xaa-Glu-Thr-Val-Gln-Asn-Leu-Ile-Lys    (SEQ ID NO:6)

Peptide 2:
Gly-Val-Thr-Val-Glu-Pro-Phe-Lys                                    (SEQ ID NO:7)

Peptide 3:
Val-Ile-Val-Asp-Ala-Tyr-Cys-Thr-Ile-Pro-Thr-Val-Asp-Ser-Lys        (SEQ ID. NO:8)

Peptide 4:
Gly-Thr-Thr-Asp-Ala-Gly-Lys-Pro-Glu-Ser-Ile-Glu-Ile-Ile-Thr-       (SEQ ID NO:9)
                                      <-----as1

Asp-Asn-Val-Asp-Glu-Asn-Leu-Thr-Lys

Peptide 5
Asn-Phe-Glu-Thr-Val-Leu-Gln-Pro-Phe-Ser-Glu-Phe-His-Asn-Arg-       (SEQ ID NO:11)

Tyr-Tyr-Lys
(Overlaps and extends the N-terminal sequence).
```

Media and other materials:
STC: 1.2 M sorbitol, 10 mM Tris-HCl, pH=7.5, 10 mM CaCl$_2$
BSA (Sigma, type H25)
Leucine-7 amido4-methylcoumarin (Sigma)
PEG 4000 (polyethylene glycol, molecular weight=4,000) (BDH, England)
Sequenase®Kit (United Stated Biochemical, USA)
Hybond-N nylon membrane (Amersham, USA)
Q-sepharose (Pharmacia Tm)
Superdex 200 Tm
Amicon membrane
VG Analytical TofSpec
α-Cyano4-hydroxycinnamic acid (Aldrich, Steinheim, Germany).
YPD: 10 g yeast extract, 20 g peptone, H$_2$O to 810 ml. Autoclaved, 90 ml 20% glucose (sterile filtered) added.
10×Basal salt: 66.8 g yeast nitrogen base, 100 g succinic acid, 60 g NaOH, H$_2$O ad 1000 ml, sterile filtered.
SC-URA: 90 ml 10×Basal salt, 22.5 ml 20% casamino acids, 9 ml 1 % tryptophan, H$_2$O ad 806 ml, autoclaved, 3.6 ml 5% threonine and 90 ml 20% glucose or 20 % galactose added.
SC-H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.
SC-H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.
YNB-1 agar: 3.3 g/l KH2PO4, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.55 ml of a 1 % L-leucine solution and 1.55 ml of a 1% histidine solution were added per 450 ml agar.
YNB-1 broth: Composition as YNB- 1 agar, but without the agar.
Minimal plates: (Cove Biochem.Biophys.Acta 113 (1966) 51–56) containing 1.0 M sucrose, pH 7.0, 10 mM acetamide as nitrogen source and 20 mM CsCl
Whey protein hydrolysate: Whey hydrolysed with Alcalase® and Neutrase® was diluted with water until the protein content was 8% (w/w) of the total solution.
Methods
RNA isolation: The total RNA was prepared, from frozen, powdered mycelium of A. oryzae A01568, by extraction with guanidinium thiocyanate followed by ultracentifuigation through a 5.7 M CsCl cushion (Chirgwin et al., (1979), Biochemistry 18, 5294–5299). The poly(A)$^+$ RNA was performed by oligo(dT)-cellulose affinity chromatography (Aviv, H, and Leder, P., (1972), Proc. Natl. Acad. Sci. U.S.A. 69, 1408–1412).

CDNA synthesis: Double-stranded cDNA was synthesized from 5 ,g of *Aspergillus oryzae* poly(A)+ RNA as described by Kofod et al., J. of Biol. Chem., (1994), 269, 29182–29189, except that 25 ng of random hexanucleotide primers (Pharmacia, Sweden) were included in the first strand synthesis. a Construction of cDNA library:

The cDNA library was constructed as described by Kofod et al., J. of Biol. Chem., (1994), 269, 29182–29189.

Transformation of *Saccharomyces cerevisiae:*

To ensure that all the bacterial clones were tested in yeast, a number of yeast transformants 5 times larger than the number of bacterial clones in the original pools was set as the limit.

One μl aliquots of purified plasmid DNA (100 ng/μl) from individual pools were electroporated (200 Ω, 1.5 kV, 24 AF) into 40 μl of competent *S. cerevisiae* cells (OD600=1.5 in 500 ml YPD, washed twice in cold distilled water, once in cold 1 M sorbitol, resuspended in 0.5 ml 1 M sorbitol, Becker & Guarante, 1991). After addition of 1 ml 1 M cold sorbitol, 80 41 aliquots were plated on SC+glucose–uracil to give 250–400 c.f.u./plate and incubated at 30° C. for 3–5 days.

Transformation of Schizosaccharomyces pombe

*Schizosaccharozyces pombe* was transformed as described by Bröker, (1987) BioTechniques, 5, 51–517.

Purification of 35 kDa aminopeptidase from *Aspergillus oryzae:*

One gram freeze dried powder of the fermentation supernatant of *Aspergillus oryzae* A01568 was dissolved in 100 ml Tris-acetate buffer (25 mM pH 8 ). Ionic strength was 2 mSi. The suspension was filtered through 45μ millipore filter. The filtered solution was applied on a 200 ml anion exchange chromatography column packed with Q-sepharose, which was equilibrated with the Tris-acetate buffer. Alkaline protease which is a major endoprotease with isoelectric point of 8 was collected in effluent. The column was washed with the Tris-acetate buffer until no more UV absorbing material was present in effluent.

The bound proteins were eluted with linear salt gradient using 0 to 0.5 M NaCl in the Tris-acetate buffer (pH 8) using 10 column volume with a flow rate of 4 ml/minutes. Fractions containing aminopeptidase activity (see below) were pooled and dialyzed against Tris-acetate buffer (25 mM , pH 6).

The dialyzed pool containing activity was adjusted to pH 6 and ionic strength to 2 mSi and applied on 50 ml High performance Q-sepharose column, equilibrated with 25 mM Tris-acetate buffer pH 6, for anion exchange chromatography. The column was then washed until the UW absorbing material in effluent was under 0.05 at 280 nm. Bound activity was then eluted with 20 column volume linear salt gradient, from 0 to 0.5 M NaCI at a flow rate of 2 ml/minutes. Fractions containing aminopeptidase activity were pooled and concentrated by ultrafiltration, using 50 mM sodium-acetate buffer (pH 6).

Two ml of the concentrated pool containing aminopeptidase activity was applied on Superdex 200 Tm column equilibrated with 50 mM sodium acetate buffer (pH 6) containing 0.1 M NaCl. The gel filtration was carried out using a flow rate of 0.5 ml/minutes. Samples containing aminopeptidase activity were pooled and concentrated by ultrafiltration using Amicon membrane with a cut-off-value of 10 kDa.

Amino acid sequence determination of N-terminal and internal peptides of the *Aspergillus oryzae* aminopeptidase:

S-carboxymethylated samples of the purified native aminopeptidase is digested with lysyl-specific protease, and the resulting peptides are separated by reverse phase high 2 ( pressure liquid chromatography (HPLC) and sequenced as described by Matsudaira, A Practical Guide to Protein and peptide Purification for Microsequencing, 3–88, Academic Press Inc, San Diego, Calif., in an Applied Biosystems 473A sequencer according to the manufacturer's instructions (Applied Biosystems).

Reagents and solvents for amino acid sequencing are from Applied Biosystems (Foster City, Calif.).

Designing of PCR primers:

The PCR primers were designed as described by Kofod et al., J. of Biol. Chem., (1994), 269, 29182–29189.

Generation of a cDNA probe for an aminopeptidase using PCR:

One μg of double stranded plasmid DNA from a cDNA library pool was PCR amplified using 500 pmol of each of the designed primers in combinations with 500 pmol of pYES 2.0 polylinker primer (forward and reverse), a DNA thermal cycler (Landgraf, Germany) and 2.5 units of Taq polymerase (Perkin-Elmer).

Thirty cycles of PCR were performed using a cycle profile of denaturation at 94° C. for 1 minute, annealing at 55° C. for 2 minutes, and extension at 72° C for 3 minutes.

Dideoxy chain-termination method:

The method was carried out as described by Sanger et al., (1977), Proc. Natl. Acad. Sci. U.S.A. 74, 5463–5467, using the Sequenase®Kit and universal pUC primers.

Characterization of positive cDNA clones by Southern blot analysis:

The positive clones were characterized by the use of Southern blot hybridization using the 0.5 kb random-primed $^{32}$P-labelled PCR-product or 35 kDa aminopeptidase as probe. The hybridizations were carried out in 2×SSC, 5×Denhardt's solution, 0.5% (w/v) SDS, 100 μg/ml denatured salmon sperm DNA for 48 hours at 65° C. followed by washing at high stringency in 2 . SSC (2×15 minutes), 2×SSC, 0.5% SDS (30 minutes), 0.2×SSC, 0.5% SDS (30 minutes) and finally in 2×SSC (15 minutes), at 65° C (Sambrook et al. (1989), supra.

Electrophoresis

Electrophoresis was performed on a 0.7% agarose gel from SeaKem, FMC.

Capillary blotting

Capillary blotting method is described by Sambrook et al., (1989), supra) using 10×SSC as transfer buffer High stringency washes of hybridized clones:

Washing was carried out in 2×15 minutes in 2×SSC, 2×30 minutes in 0.1×SSC, 0.5% SDS and 15 minutes in 2×SSC, at 65° C.

Transformation of *Aspergillus oryzae:*

Transformation of *Aspergillus oryzae* was carried out as described by Christensen et al., (1988), *Biotechnology* 6, 1419–1422.

Construction of the aminopeptidase expression cassette for Aspergillus

Plasmid DNA was isolated from the positive *E. coli* clones using standard procedures and analyzed by restriction enzyme analysis. The cDNA insert was excised using appropriate restriction enzymes and ligated into an Aspergillus expression vector.

Transformation of *Aspergilus oryzae* or *Aspergilus niger* (general procedure)

100 ml of YPD (Sherman et al., Methods in Yeast Genetics, Cold Spring Harbor Laboratory, 1981) is inoculated with spores of *A. oryzae* or *A. niger* and incubated with shaking at 37° C. for about 2 days. The mycelium is harvested by filtration through miracloth and washed with 200 ml of 0.6 M MgSO$_4$. The mycelium is suspended in 15 ml of 1.2 M MgSO$_4$. 10 mM NaH$_2$PO$_4$, pH=5.8. The suspension is cooled on ice and 1 ml of buffer containing 120 mg of Novozym® 234 is added. After 5 minutes 1 ml of 12 mg/ml BSA is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6 M sorbitol, 100 mM Tris-HCl, pH=7.0. Centrifugation is performed for 15 minutes at 100 g and the protoplasts are collected from the top of the MgSO$_4$ cushion. 2 volumes of STC are added to the protoplast suspension and the mixture is centrifugated for 5 minutes at 1000 g. The protoplast pellet is resuspended in 3 ml of STC and repelleted. This is repeated.

Finally the protoplasts are resuspended in 0.2-1 ml of STC.

100 μl of protoplast suspension is mixed with 5–25 μg of the appropriate DNA in 10 μl of STC. Protoplasts are mixed with p3SR2 (an *A. nidulans* amdS gene carrying plasmid). The mixture is left at room temperature for 25 minutes. 0.2 ml of 60% PEG 4000. 10 mM CaCl$_2$ and 10 mM Tris-HCl, pH 7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on the appropriate plates. Protoplasts are spread on minimal plates to inhibit background growth. After incubation for 4–7 days at 37° C. spores are picked and spread for single colonies. This procedure is repeated and spores of a single colony after the second re-isolation is stored as a defined transformant.

Purification of the *Aspergillus oryzae* transformants:

*Aspergillus oryzae* colonies are purified through conidial spores on AmdS$^+$-plates (+0,01% Triton X-100) and growth in YPM for 3 days at 30° C.

Identification of aminopeptidase positive *Aspergilus oryzae* transformants:

The supernatants from the *Aspergillus oryzae* transformants were assayed for aminopeptidase on agar plates overlayered with 60 μg/ml of Leucine-7 amido-4-methylcoumarin. Positive transformants were identified by analyzing the plates by fluorescence under UV-light after 5 minutes to 2 hours incubation at 30° C.

SDS-PAGE analysis:

SDS-PAGE analysis of supernatant from an *Aspergillus oryzae* aminopeptidase producing transformant. The transformant was grown in 5 ml YPM for three days. 10 μl of supernatant was applied to 12 % SDS-polyacrylamide gel which was subsequently stained with Coomassie Brilliant Blue.

Mass spectrometry

Mass spectrometry is done using matrix assisted laser desorption ionisation time-of flight mass spectrometry in a VG Analytical TofSpec. For mass spectrometry 2 μl of sample is mixed with 2 μl saturated matrix solution (α-cyano-4-hydroxycinnamic acid in 0.1% TFA:acetonitrile (70:30)) and 2 μl of the mixture spotted onto the target plate. Before introduction into the mass spectrometer the solvent was removed by evaporation. Samples are desorbed and ionised by 4 ns laser pulses (337 un) at threshold laser power and accelerated into the field-free flight tube by an accelerating voltage of 25 kV. Ions were detected by a micro channel plate set at 1850 V. The spectra is calibrated externally with proteins of known mass.

Immunological cross-reactivity:

Antibodies to be used in determining immunological cross-reactivity may be prepared by use of a purified aminopeptidase. More specifically, antiserum against the aminopeptidase of the invention may be raised by immunizing rabbits (or other rodents) according to the procedure described by N. Axelsen et al. in: A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically pp. 27–31). Purified immunoglobulins may be obtained from the antisera, for example by salt precipitation ((NH$_4$)2 SO$_4$), followed by dialysis and ion exchange chromatography, e.g. on DEAE-Sephadex. Immunochemical characterization of proteins may be done either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., suMra, Chapters 3 and 4), or by rocket immunoelectrophoresis (N. Axelsen et al., Chapter 2).

Southern blot analysis:

Genomic DNA from *A. oryzae* is isolated according to Yelton et al., (1984), Proc. Natl. Acad. Sci. U.S.A. 81., p. 1470–1474, and digested to completion with BamHI, BglII, EcoRI and HindIII (10 μg/sample), fractionated on a 0.7% agarose gel, denatured and blotted to a nylon filter (Hybond-N) using 10×SSC as transfer buffer (Southern, E. M., (19947 75), J. Mol. Biol. 98, p. 503–517). The aminopeptidase cDNA is $^{32}$P-labeled (>1×10$^9$ cpm/μg) by random-priming and used as a probe in Southern analysis. The hybridization and washing conditions are as described in RNA gel blot analysis. The filter is autoradiographed at −80° C. for 12 hours.

RNA gel blot analysis:

Poly(A)$^+$ RNA (1 μg) from *A. oryzae* is electrophoresed in 1.2 % agarose-2.2 M formaldehyde gels (Thomas, P. S., (1983) Methods Enzymol. 100, pp. 255–2663) and blotted to a nylon membrane (Hybond-N) with 10×SSC as transfer buffer. The aminopeptidase cDNA is $^{32}$P-labeled (>1×10$^9$ cpm/μg ) by random priming and hybridized to the membrane for 18–20 hours at 65° C. in 5×SSC, 5×Denhardt's solution, 0.5% SDS (w/v) and 100 μg/ml denatured salmon sperm DNA. The filter is washed in 5×SSC at 65° C. (2×15 minutes), 2×SSC, 0.5% SDS (1×30 minutes), 0.2×SSC, 0.5 % SDS (1×30 minutes), and 5×SSC (2×15 minutes). The filter is autoradiographed at −80° C. for 12 hours.

Determination of aminopeptidase activity (LAPU)

One LAPU is defined as the amount of enzyme which hydrolyzes 1 μmole of L-leucine-p-nitroanilide per minute using the method described in AF 298/1-GB (available on request from Novo Nordisk A/S).

% DH determination based on TMBS analysis

The extent of protein hydrolysis may be determined by the degree of hydrolysis achieved. In the context of this invention, the degree of hydrolysis (DH) is defined by the following formula:

$$DH = \frac{h}{h_{total}} \times 100\%$$

h is the number of peptide bonds hydrolysed and $h_{total}$ is the total number of peptide bonds in the protein. $h_{total}$ is dependent on the type of raw material, whereas h can be expressed as a function of meqv leucine NH$_2$, measured by for instance TNBS-analyses Determination of % DH is described in EF-9415317 (available on request from Novo Nordisk A/S)

Testing of Doughs and Breads

According to the present invention the effect of adding a single component enzyme with aminopeptidase activity may be tested in doughs and breads by using the following method:

Preparation of Breads

Procedure:
1. Dough mixing (Spiral mixer)
   3 min. at 700 RPM
   5 min. at 1400 RPM the mixing time is predetermined and adjusted by a skilled baker based on the flour used so as to obtain an optimum dough consistency under the testing conditions used.
2. 1st proof: 30° C.-80% RH, 15 min.
3. Scaling and shaping;
4. Resting for 5-minutes at ambiant temperature;
5. Final proof: 32° C.-80% RH, 45 minutes for rolls, 55 minutes for bread;
6. Baking: 225° C., 22 minutes for rolls and 30 minutes for loaf.

Evaluation of Dough and Baked Products

Dough and baked products may be evaluated as follows: Loaf specific volume: the mean value of 4 loaves volume are measured using the traditional rape seed method. The specific volume is calculated as volume ml per g bread. The specific volume of the control (without enzyme) is defined as 100. The relative specific volume index is calculated as:

$$\text{Specific vol. index} = \frac{\text{specific vol. of 4 loaves}}{\text{spec. vol. of 4 control loaves}} * 100.$$

The dough stickiness and crumb structure may be evaluated visually according to the following scale:

| Dough stickiness: | almost liquid | 1 |
| --- | --- | --- |
| | too sticky | 2 |
| | sticky | 3 |
| | acceptable | 3.5 |
| | normal | 4 |
| | dry | 5 |
| Crumb structure: | very poor | 1 |
| | poor | 2 |
| | non-uniform | 3 |
| | uniform/good | 4 |
| | very good | 5 |

Shock test: After the second proof a pan containing the dough is dropped from a height of 20 cm. The dough is baked and the volume of the resulting bread is determined.

Yeasty Flavour

| as control | 3 |
| --- | --- |
| slightly improved | 3.5 |
| Improved | 4 |

Crumb colour

The crumb colour is determined visually

EXAMPLES

Example 1

Construction of cDNA library

Total RNA was extracted from *Aspergillus oryzae* A01568. Poly(A)+RNA was isolated by oligo(dT)-cellulose affinity chromatography and double stranded cDNA (ds cDNA) was synthesized.

A cDNA library from *Aspergillus oryzae* A01568 consisting of $3.5 \times 10^6$ clones was constructed into the yeast expression vector pYES 2.0.

Example 2

Amplification and characterization of cDNA clones.

The aminopeptidase was purified from *Aspergillus oryzae* A01568 as described above in the section "Materials and Methods".

A long $NH_2$-terminal sequence and four internal sequences (including Peptide 1 to 5) of the aminopeptidase were obtained by digestion of S-carboxymethylated purified protein with a lysyl-specific protease.

Based on these sequences three primers were synthesized (as1, s2 and s3, respectively). Double stranded cDNA (ds cDNA) was used as template in the PCR amplification experiment as described above in the section "Materials and Methods".

Analysis of the resulting PCR-products revealed a 0.5 kb fragment with one primer pair (primer s3 and primer as1).

The PCR-fragment was sub-cloned into SmaI-cut dephosphorylated pUC 18 vector and sequenced from both ends using the Dideoxy chain-termination method as described above in the section "Material and Methods".

In addition to the primer encoded residues, the sequence of Peptide 2 obtained from the purified aminopeptidase, aligned with the deduced amino acid sequence, confirmed that the desired cDNA species had been specifically PCR amplified.

Example 3

Screening of the cDNA library for clones encoding the aminopeptidase from *Aspergillus oryzae*

Approximately 10,000 colonies from the cDNA library from *Aspergillus oryzae* A01568 were screened by colony hybridization as described above. This yielded positive clones with inserts ranging from 650 bp to 1.5 kb.

The positive clones were analyzed by Southern blot analysis as described above in the section "Materials and Methods".

Purified plasmid DNA (about 1 $\mu$g) from the aminopeptidase cDNA clones was digested to completion by HindIII and XbaI to release the cDNA inserts from the pYES vector. The samples were electrophoresed and transferred to a Hybond-N nylon membrane by the capillary blotting method. The filters were washed at high stringency resulting in positive clones with inserts ranging from 900 bp to 1700 bp.

Strongly hybridizing clones were analyzed by sequencing the ends of the cDNAs with forward and reverse pYES primers.

Analysis of the sequence data showed that some of these clones were truncated cDNAs whereas others appeared to be full-length clones. The nucleotide sequence and deduced amino acid sequence of one of the full-length clones (pC1EXP3) obtained (shown in FIG. 1) contains a cDNA insert of 1.4 kb.

Example 4

Expression of the amino-eptidase in *Aspergillus oryzae*

To obtain high level production of aminopeptidase in *Aspergillus oryzae*, the cDNA insert from the pC1EXP3 clone was sub-cloned into pHD423 and co-transformed with the AmdS+ plasmid into *Aspergillus oryzae* as described above.

The 1.4 kb cDNA insert from pC1EXP3 was isolated from pYES 2.0 by Hind III and Not I digestion, ligated to a Not I/Hind III cleaved pHD 423 vector, and transformed into *E. coli*.

The resulting transformants were purified twice (see above) and assayed for aminopeptidase activity as described above.

Transformant pA3EXP3/1 showed detectable aminopeptidase activity.

Example 5
Expression level of aminopeptidase producing transformant (DA3EXP3/1)

The amount and purity (level of expression) of secreted aminopeptidase from the transformant (pA3EXP3/1) was determined semi-quantitatively by SDS-PAGE using the non-transformed *A. oryzae* strain A01560 as a negative control and the *A. oryzae* A01568 strain as positive control (see FIG. 1).

A 36–37 kDa polypeptide could be seen in pA3EXP3/1, not present in the negative control. The size of the recombinant aminopeptidase is approximately 2 kDa higher than that of the native aminopeptidase (a double band of about 35 kDa), possibly due to additional glycosylation or other types of post-translational modifications.

Example 6

Mass spectrometry showed that the recombinant aminopeptidase is glycosylated as the mass determined exceed the mass of the polypeptide calculated from the cDNA sequence to be 32.4 kDa. The average mass of the recombinant aminopeptidase is 34.1 kDa with the masses ranging from 33 kDa to 35 kDa.

The apparent molecular weight (Me) determined by SDS-PAGE (as described in "Materials and Methods" was found to be about 35 kDa.

Example 7
Fermentation of 35 kDa aminopeptidase producing transformant

The *Aspergillus oryzae* transformant pA3EXP3/1 was grown in one liter shake flasks containing 150 ml DAP 2C (pH=5.9) for three days at 30° C.

The amount of secreted aminopeptidase was estimated by SDS-PAGE analysis to approximately 0.5 g/liter supernatant.

Example 8
Expression of 35 kDa aminopeptidase clones in *S. pombe*

The full-length 35 kDa aminopeptidase cDNA clone pC1EXP3 was re-transformed into *Schizosaccharomyces pombe* by electroporation. The 1.4 kb cDNA insert was released from the pYES 2.0 vector by SpeI and NotI digestion and subcloned into the SpeI/NotI cleaved yeast expression vector pP1, which is an *E. coli/S. pombe* shuttle vector containing the ADH promoter, and assayed for aminopeptidase activity.

It was shown that one *S. pombe* transformant had strong aminopeptidase activity, indicating that *S. pombe* is able to synthesize and secrete a functionally active 35 kDa aminopeptidase from *Aspergillus oryzae* A01568.

Example 9
Organization and Expression of the Aminopeptidase gene

The copy number of the aminopeptidase gene in the *A. oryzae* A01568 genome was determined by Southern blot hybridization described in the "Materials and Methods" section. Total DNA isolated from *A. oryzae* was digested to completion with BamHI, BglII, EcoRI or HindIII and hybridized with the aminopeptidase cDNA. The aminopeptidase probe detects only single strongly hybridizing fragments in each case except in BamHI digestion, which gives two hybridizing fragments due to a BamHI site at nucleotide position 640. This indicates that the aminopeptidase gene is present as a single copy in the *A. oryzae* A01568 genome.

Example 10

To study the expression of the 35 kDa aminopeptidase gene, poly (A)+ RNA extracted from *A. oryzae* A01568 mycelium was subjected to Northern blot analysis. Probing of the blotted RNA with the aminopeptidase cDNA revealed two species of mRNA of approximately 1.45 and 1.55 kilobases. These two mRNAs do not appear to represent transcripts of two distinct genes since the same pattern of hybridization was observed when the filters were washed at high stringency. The difference in size of the two mRNAs could be due to different lengths of 3' untranslated region, because of two polyadenylation sites, in accordance with the two cDNA species isolated from the *Aspergillus oryzae* cDNA library, one corresponding to clones pC1EXP3 and another one corresponding to pC1EXP4, which is 120 bp shorter. Both mRNAs encode the same aminopeptidase.

Example 11
Removing bitter taste from whey protein hydrolysate

The fermentation broth of Aspergillus oryzae transformant pA3EXP3/1 was tested for the ability to debitter a solution containing 8% (w/w) protease hydrolysed whey protein.

The aminopeptidase activity of fermentation broth was 5.58 LAPU/g.

The substrate protein solution was tested in flasks containing 100 g of the 8% protein hydrolysate. The fermentation broth exhibiting aminopeptidase activity was added until the relationship between enzyme and substrate (E/S) was 0.25%, calculated on the basis of a product with 5000 LAPU/g (equivalent to 12.5 LAPU/g protein), and was then re-hydrolysed for 6 hours at 50° C, pH 7.0.

The pH and the osmolarity was determined (using standard methods) after 1 minute and 6 hours, respectively. % DH was determined using the TNSB-method (described above) and % FAA (% free amino acids) was determined using standard methods.

| Aminopeptidase | pH after 1 minute | pH after 6 hours | Increase mOsm | % DH by TNBS-method | total % FAA |
|---|---|---|---|---|---|
| Transformant | 6.47 | 6.65 | 59 | 7.01* | 13 |
| Blind | 6.61 | 6.81 | 1 | | 3 |

*the increase of DH caused by the hydrolysis of the substrate by the ammopeptidase. DH of the blind is 28%

A sample of debittered hydrolysate containing 13% FFA was analyzed for the content of leucine. It was found that leucine constituted about 2.7%. while leucine constituted about 0.3% of the blind.

Example 12
Taste test

The taste of debittered protein hydrolysate was assessed by a tasting panel of 5 persons using a Bitterness Index (BI) between 0 (not bitter) and 10 (blind).

The bitterness, of a sample of bitter tasting 3.5% protein hydrolysate (blind) and a similar sample subjected to the transformant, was assessed.

The Bitterness Index (BI) for the protein hydrolysate sample subjected to the transformant was found to be in the range of about 6.2.

This result shows that the 35 kDa aminopeptidase had debittered the protein hydrolysate samples.

Example 13
Bread flavor, dough stickiness and crumb structure

The flavour, dough stickiness and crumb structure of bread prepared using from 0 to 300 LAPU per kg flour were compared with bread prepared using the commercial product Flavourzyme®. The bread were prepared and assessed as described above in the "Material and Methods" section.

The following result (average of duplication) were found:

| Enzyme(s) | LAPU/kg flour | Avg. vol. Index | Flavour | Dough stickiness | Crumb structure |
|---|---|---|---|---|---|
| Flavourzyme ® | 80 | 112 | 4 | 3 | crumby and open |
| Enzyme of the Invention | 0 | 100 | 3 | 4 | as control |
| | 10 | 100 | 3 | 4 | as control |
| | 30 | 100 | 3 | 4 | as control |
| | 50 | 100 | 3.25 | 4 | as control |
| | 80 | 98 | 3.5 | 4 | as control |
| | 100 | 102 | 3.5 | 4 | as control |
| | 150 | 97 | 4 | 4 | as control |
| | 200 | 99 | 4 | 4 | as control |
| | 300 | 100 | 4 | 4 | as control |

As can be seen from the above table the 35 kDa aminopeptidase of the invention gives a significant flavour enhancement in the form of a "fresh baked" bread smell when added in amounts from 30 to 300 LAPU per kg flour. The crumb structure is not affected by the aminopeptidase of the invention. The dough stickiness is improved in comparison to the commercial protease/peptidase complex Flavourzyme®.

As will be apparent to those skilled in the art in the light of the foregoing disclosure, many alterations and modifications are possible in the practice of this invention without departing from the-spirit or scope thereof. Accordingly, the scope of the invention is to be construed in accordance with the substance defined by the claims below.

---

What is claimed is:

1. An isolated enzyme exhibiting aminopeptidase activity which is encoded by a DNA sequence that hybridizes to SEQ ID NO. 1 under the following conditions: hybridizing in 2×SSC, 5×Denhardt's solution, 0.5% SDS, 100 μg/ml denatured salmon sperm DNA for 48 hours at 65° C. followed by washing at 65° C. in 2×SSC, 0.5% SDS in 2×SSC, 0.5% SDS in 0.2×SSC, and 2×SSC.

2. The enzyme of claim 1 wherein the DNA sequence is derived from a strain of Aspergillus.

3. The enzyme of claim 2 wherein the DNA sequence is derived from a strain of *Aspergillus oryzae*.

4. The enzyme of claim 1 wherein the DNA sequence is derived from a strain of Trichoderma, Penicillium, Fusarium, or Humicola.

5. The enzyme of claim 1, wherein the enzyme comprises a molecular weight of about 35 kDa determined by SDS-PAGE.

6. An enzyme preparation comprising the enzyme of claim 1.

7. A bread-improving or a dough-improving composition comprising the enzyme of claim 1.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 1409 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (B) STRAIN: Aspergillus oryzae A01568

(ix) FEATURE:
      (A) NAME/KEY: CDS
      (B) LOCATION:52..1183

(xi) SEQUENCE DESCRIPTION: SEQ ID NO: 1:

```
CGAGCATTCC GTTCGTATCG ACTTGGTGGT ACACGCTTTC GTTCTCTCAA G ATG CGT        57
                                                         Met Arg
                                                           1

TTC CTC CCC TGC ATC GCG ACT TTG GCA GCC ACG GCC TCT GCC CTT GCT       105
Phe Leu Pro Cys Ile Ala Thr Leu Ala Ala Thr Ala Ser Ala Leu Ala
          5                  10                  15

ATT GGA GAC CAT GTA CGC TCG GAC GAT CAG TAT GTC CTA GAA CTC GCC       153
Ile Gly Asp His Val Arg Ser Asp Asp Gln Tyr Val Leu Glu Leu Ala
     20                  25                  30

CCG GGA CAA ACG AAA GTT GTG ACG GAA GCA GAG AAA TGG GCT CTG AGA       201
Pro Gly Gln Thr Lys Val Val Thr Glu Ala Glu Lys Trp Ala Leu Arg
 35                  40                  45                  50

GCT GAG GGC AAG CGT TTC TTC GAT ATA ACC GAA CGG GCC AGT AGC CTG       249
Ala Glu Gly Lys Arg Phe Phe Asp Ile Thr Glu Arg Ala Ser Ser Leu
                 55                  60                  65

GAA CTC GCA TCG AAC AAG AAA CAA AAG CTC GCG GTT ACC TAC CCC GAT       297
Glu Leu Ala Ser Asn Lys Lys Gln Lys Leu Ala Val Thr Tyr Pro Asp
             70                  75                  80
```

```
TCC GTG CAA CAC AAC GAG ACC GTG CAA AAT CTG ATC AAG TCG CTC GAC      345
Ser Val Gln His Asn Glu Thr Val Gln Asn Leu Ile Lys Ser Leu Asp
            85                  90                  95

AAA AAG AAC TTC GAA ACC GTT CTC CAG CCG TTC TCG GAG TTC CAC AAT      393
Lys Lys Asn Phe Glu Thr Val Leu Gln Pro Phe Ser Glu Phe His Asn
100                 105                 110

CGC TAT TAC AAG AGC GAC AAT GGC AAG AAA TCA TCC GAG TGG CTG CAA      441
Arg Tyr Tyr Lys Ser Asp Asn Gly Lys Lys Ser Ser Glu Trp Leu Gln
115                 120                 125                 130

GGC AAG ATT CAG GAA ATC ATC TCC GCC AGT GGA GCA AAG GGA GTC ACT      489
Gly Lys Ile Gln Glu Ile Ile Ser Ala Ser Gly Ala Lys Gly Val Thr
                135                 140                 145

GTG GAG CCT TTC AAA CAC TCC TTC CCG CAG TCG AGT CTG ATT GCG AAA      537
Val Glu Pro Phe Lys His Ser Phe Pro Gln Ser Ser Leu Ile Ala Lys
            150                 155                 160

ATC CCC GGC AAG AGT GAC AAG ACC ATC GTG CTT GGA GCG CAT CAG GAC      585
Ile Pro Gly Lys Ser Asp Lys Thr Ile Val Leu Gly Ala His Gln Asp
            165                 170                 175

TCC ATC AAC CTT GAT TCA CCC TCA GAG GGC CGT GCA CCG GGA GCT GAT      633
Ser Ile Asn Leu Asp Ser Pro Ser Glu Gly Arg Ala Pro Gly Ala Asp
180                 185                 190

GAC GAT GGA TCC GGC GTT GTT ACC ATT CTC GAA GCC TTC CGC GTT CTC      681
Asp Asp Gly Ser Gly Val Val Thr Ile Leu Glu Ala Phe Arg Val Leu
195                 200                 205                 210

CTG ACG GAC GAG AAG GTC GCA GCC GGT GAG GCT CCG AAC ACC GTT GAG      729
Leu Thr Asp Glu Lys Val Ala Ala Gly Glu Ala Pro Asn Thr Val Glu
                215                 220                 225

TTC CAC TTC TAT GCC GGA GAG GAG GGT GGT CTG CTG GGA AGT CAG GAC      777
Phe His Phe Tyr Ala Gly Glu Glu Gly Gly Leu Leu Gly Ser Gln Asp
            230                 235                 240

ATC TTC GAG CAG TAC TCG CAG AAA AGC CGA GAC GTG AAA GCC ATG CTT      825
Ile Phe Glu Gln Tyr Ser Gln Lys Ser Arg Asp Val Lys Ala Met Leu
            245                 250                 255

CAA CAG GAT ATG ACG GGT TAT ACT AAA GGC ACA ACC GAT GCT GGA AAG      873
Gln Gln Asp Met Thr Gly Tyr Thr Lys Gly Thr Thr Asp Ala Gly Lys
            260                 265                 270

CCG GAG TCG ATC GGT ATC ATC ACT GAC AAT GTC GAT GAG AAC CTG ACC      921
Pro Glu Ser Ile Gly Ile Ile Thr Asp Asn Val Asp Glu Asn Leu Thr
275                 280                 285                 290

AAG TTC CTG AAG GTC ATT GTC GAT GCT TAT TGC ACT ATC CCG ACC GTC      969
Lys Phe Leu Lys Val Ile Val Asp Ala Tyr Cys Thr Ile Pro Thr Val
                295                 300                 305

GAT TCG AAA TGC GGA TAC GGA TGC TCT GAC CAT GCT TCT GCC ACG AAG     1017
Asp Ser Lys Cys Gly Tyr Gly Cys Ser Asp His Ala Ser Ala Thr Lys
            310                 315                 320

TAT GGT TAT CCC GCC GCA TTC GCA TTC GAG TCA GCC TTT GGC GAC GAC     1065
Tyr Gly Tyr Pro Ala Ala Phe Ala Phe Glu Ser Ala Phe Gly Asp Asp
            325                 330                 335

AGC CCT TAC ATT CAC TCG GCT GAT GAT ACG ATT GAG ACC GTC AAC TTT     1113
Ser Pro Tyr Ile His Ser Ala Asp Asp Thr Ile Glu Thr Val Asn Phe
            340                 345                 350

GAC CAT GTG CTG CAA CAC GGC AAA CTG ACT CTT GGA TTT GCA TAT GAG     1161
Asp His Val Leu Gln His Gly Lys Leu Thr Leu Gly Phe Ala Tyr Glu
355                 360                 365                 370

CTT GCC TTC GCA GAT TCG CTG T AAGGCTTATG ACGACGGTTG TATGAGCGAG      1213
Leu Ala Phe Ala Asp Ser Leu
                375

AGATCCAGTC CAACAGTGTG TATAATATGT GGGCCCGTGT TCAAATAGCA CTTTGATTTA   1273

GCCAGTGAGT AGCTTTGGTG GCGAAAATGG AGGCCGAATT CTAGGCAACA TCGAACTGGA   1333
```

```
GGCTGTCAGG GGCGCATCAC AAGAAGTTTT GAGCTACATA AGCGAGATAA AAGTCAGAAA    1393

AAAAAAAAAA AAAAAA                                                    1409
```

(2) INFORMATION FOR SEQ ID NO: 2:

(i) SEQUENCE CHARACTERISTICS:
        (A) LENGTH: 377 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Arg Phe Leu Pro Cys Ile Ala Thr Leu Ala Ala Thr Ala Ser Ala
 1               5                  10                  15

Leu Ala Ile Gly Asp His Val Arg Ser Asp Asp Gln Tyr Val Leu Glu
            20                  25                  30

Leu Ala Pro Gly Gln Thr Lys Val Val Thr Glu Ala Glu Lys Trp Ala
        35                  40                  45

Leu Arg Ala Glu Gly Lys Arg Phe Phe Asp Ile Thr Glu Arg Ala Ser
    50                  55                  60

Ser Leu Glu Leu Ala Ser Asn Lys Lys Gln Lys Leu Ala Val Thr Tyr
65                  70                  75                  80

Pro Asp Ser Val Gln His Asn Glu Thr Val Gln Asn Leu Ile Lys Ser
                85                  90                  95

Leu Asp Lys Lys Asn Phe Glu Thr Val Leu Gln Pro Phe Ser Glu Phe
            100                 105                 110

His Asn Arg Tyr Tyr Lys Ser Asp Asn Gly Lys Lys Ser Ser Glu Trp
        115                 120                 125

Leu Gln Gly Lys Ile Gln Glu Ile Ile Ser Ala Ser Gly Ala Lys Gly
    130                 135                 140

Val Thr Val Glu Pro Phe Lys His Ser Phe Pro Gln Ser Ser Leu Ile
145                 150                 155                 160

Ala Lys Ile Pro Gly Lys Ser Asp Lys Thr Ile Val Leu Gly Ala His
                165                 170                 175

Gln Asp Ser Ile Asn Leu Asp Ser Pro Ser Glu Gly Arg Ala Pro Gly
            180                 185                 190

Ala Asp Asp Asp Gly Ser Gly Val Val Thr Ile Leu Glu Ala Phe Arg
        195                 200                 205

Val Leu Leu Thr Asp Glu Lys Val Ala Ala Gly Glu Ala Pro Asn Thr
    210                 215                 220

Val Glu Phe His Phe Tyr Ala Gly Glu Glu Gly Leu Leu Gly Ser
225                 230                 235                 240

Gln Asp Ile Phe Glu Gln Tyr Ser Gln Lys Ser Arg Asp Val Lys Ala
                245                 250                 255

Met Leu Gln Gln Asp Met Thr Gly Tyr Thr Lys Gly Thr Thr Asp Ala
            260                 265                 270

Gly Lys Pro Glu Ser Ile Gly Ile Ile Thr Asp Asn Val Asp Glu Asn
        275                 280                 285

Leu Thr Lys Phe Leu Lys Val Ile Val Asp Ala Tyr Cys Thr Ile Pro
    290                 295                 300

Thr Val Asp Ser Lys Cys Gly Tyr Gly Cys Ser Asp His Ala Ser Ala
305                 310                 315                 320

Thr Lys Tyr Gly Tyr Pro Ala Ala Phe Ala Phe Glu Ser Ala Phe Gly
                325                 330                 335
```

```
Asp Asp Ser Pro Tyr Ile His Ser Ala Asp Asp Thr Ile Glu Thr Val
            340                 345                 350

Asn Phe Asp His Val Leu Gln His Gly Lys Leu Thr Leu Gly Phe Ala
            355                 360                 365

Tyr Glu Leu Ala Phe Ala Asp Ser Leu
            370                 375
```

(2) INFORMATION FOR SEQ ID NO: 3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Primer (iii) HYPOTHETICAL: NO (iv) ANTI-SENSE: YES (xi) SEQUENCE DESCRIPTION: SEQ ID NO: 3:

TCNACRTTRT CNGTNATNAT YTCNAT                                      26

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Primer (iii) HYPOTHETICAL: NO (iv) ANTI-SENSE: NO (xi) SEQUENCE DESCRIPTION: SEQ ID NO: 4:

GARACNGTNC ARAAYCTNAT                                            20

(2) INFORMATION FOR SEQ ID NO: 5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Primer (iii) HYPOTHETICAL: NO (iv) ANTI-SENSE: NO (xi) SEQUENCE DESCRIPTION: SEQ ID NO: 5:

GAYAARAARA AYTTYGAWAC NGT                                       23

(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 6:

Tyr Pro Asp Ser Val Gln His Xaa Glu Thr Val Gln Asn Leu Ile Lys
1               5                   10                  15

(2) INFORMATION FOR SEQ ID NO: 7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 7:

Gly Val Thr Val Glu Pro Phe Lys
1               5

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 8:

Val Ile Val Asp Ala Tyr Cys Thr Ile Pro Thr Val Asp Ser Lys
1               5                   10                  15

(2) INFORMATION FOR SEQ ID NO: 9:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 9:

Gly Thr Thr Asp Ala Gly Lys Pro Glu Ser Ile Glu Ile Ile Thr Asp
1               5                   10                  15
Asn Val Asp Glu Asn Leu Thr Lys
            20

(2) INFORMATION FOR SEQ ID NO: 10:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 10:

```
Tyr Pro Asp Ser Val Gln His Xaa Glu Thr Val Gln Asn Leu Ile Lys
1               5                   10                  15
Ser Leu Asp Lys Lys Asn Phe Glu Thr Val Leu Gln Pro
            20                  25
```

(2) INFORMATION FOR SEQ ID NO: 11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 11:

```
Asn Phe Glu Thr Val Leu Gln Pro Phe Ser Glu Phe His Asn Arg Tyr Tyr Lys
1               5                   10                  15
```

(2) INFORMATION FOR SEQ ID NO:12:

(i) SEQUENCE CHARACTERISTICS:
        (A) LENGTH: 1272 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (B) STRAIN: Aspergillus oryzae A01568

(xi) SEQUENCE DESCRIPTION: SEQ ID NO: 12:

```
CTCGAGCATT CCGTTCGTAT CGACTTGGTG GTACACGCTT TCGTTCTCTC AAGATGCGTT      60
TCCTCCCCTG CATCGCGACT TTGGCAGCCA CGGCCTCTGC CCTTGCTATT GGAGACCATG     120
TACGCTCGGA CGATCAGTAT GTCCTAGAAC TCGCCCCGGG ACAAACGAAA GTTGTGACGG     180
AAGCAGAGAA ATGGGCTCTG AGAGCTGAGG GCAAGCGTTT CTTCGATATA ACCGAACGGG     240
CCAGTAGCCT GGAACTCGCA TCGAACAAGA AACAAAAGCT CGCGGTTACC TACCCCGATT     300
CCGTGCAACA CAACGAGACC GTGCAAAATC TGATCAAGTC GCTCGACAAA AAGAACTTCG     360
AAACCGTTCT CCAGCCGTTC TCGGAGTTCC ACAATCGCTA TTACAAGAGC GACAATGGCA     420
AGAAATCATC CGAGTGGCTG CAAGGCAAGA TTCAGGAAAT CATCTCCGCC AGTGGAGCAA     480
AGGGAGTCAC TGTGGAGCCT TTCAAACACT CCTTCCCGCA GTCGAGTCTG ATTGCGAAAA     540
TCCCCGGCAA GAGTGACAAG ACCATCGTGC TTGGAGCGCA TCAGGACTCC ATCAACCTTG     600
ATTCACCCTC AGAGGGCCGT GCACCGGGAG CTGATGACGA TGGATCCGGC GTTGTTACCA     660
TTCTCGAAGC CTTCCGCGTT CTCCTGACGG ACGAGAAGGT CGCAGCCGGT GAGGCTCCGA     720
ACACCGTTGA GTTCCACTTC TATGCCGGAG AGGAGGGTGG TCTGCTGGGA AGTCAGGACA     780
TCTTCGAGCA GTACTCGCAG AAAAAGCCGA GACGTGAAAGC CATGCTTCAA CAGGATATGA     840
```

```
                                                           -continued

CGGGTTATAC TAAAGGCACA ACCGATGCTG GAAAGCCGGA GTCGATCGGT ATCATCACTG    900

ACAATGTCGA TGAGAACCTG ACCAAGTTCC TGAAGGTCAT TGTCGATGCT TATTGCACTA    960

TCCCGACCGT CGATTCGAAA TGCGGATACG GATGCTCTGA CCATGCTTCT GCCACGAAGT   1020

ATGGTTATCC CGCCGCATTC GCATTCGAGT CAGCCTTTGG CGACGACAGC CCTTACATTC   1080

ACTCGGCTGA TGATACGATT GAGACCGTCA ACTTTGACCA TGTGCTGCAA CACGGCAAAC   1140

TGACTCTTGG ATTTGCATAT GAGCTTGCCT TCGCAGATTC GCTGTAAGGC TTATGACGAC   1200

GGTTGTATGA GCGAGAGATC CAGTCCAACA GTGTGTATAA TATGTGGGCC CGTGTTCAAA   1260

TAGCACTTAA AA                                                       1272

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

GARACNGTNC ARAAYCTNAT                                                 20

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

GAYAARAARA AYTTYGANAC NGT                                             23

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TCNACRTTRT CNGTNATNAT YTCNAT                                          26
```